United States Patent [19]

Hsu

[11] Patent Number: 5,078,886

[45] Date of Patent: Jan. 7, 1992

[54] SEPARATION OF MIXTURES BY TWO-PHASE SYSTEMS

[75] Inventor: James T. Hsu, Bethlehem, Pa.

[73] Assignee: Lehigh University, Bethlehem, Pa.

[21] Appl. No.: 591,832

[22] Filed: Oct. 2, 1990

Related U.S. Application Data

[63] Continuation-in-part of Ser. No. 423,333, Oct. 18, 1989, Pat. No. 4,980,065.

[51] Int. Cl.$^5$ .............................................. B01D 11/04
[52] U.S. Cl. .................................... 210/632; 210/634; 210/635; 435/280; 562/401
[58] Field of Search ............... 210/632, 634, 635, 636; 435/280; 562/401

[56] References Cited

U.S. PATENT DOCUMENTS

| | | | |
|---|---|---|---|
| 3,980,665 | 9/1976 | Fahmenstich et al. | 562/401 |
| 4,318,819 | 3/1982 | Malloy et al. | 210/635 |
| 4,318,820 | 3/1982 | Malloy et al. | 210/635 |
| 4,322,310 | 3/1982 | House | 210/635 |
| 4,324,681 | 4/1982 | House | 210/635 |
| 4,481,362 | 11/1984 | Nakai et al. | 435/280 |
| 4,519,955 | 5/1985 | Chibata et al. | 562/401 |
| 4,579,661 | 4/1986 | Gustafsson | 210/635 |
| 4,610,820 | 9/1986 | Christensen et al. | 540/200 |
| 4,610,827 | 9/1986 | Yukawa et al. | 562/401 |
| 4,636,470 | 1/1987 | Empie | 435/280 |
| 4,670,395 | 6/1987 | Kung et al. | 435/280 |
| 4,855,446 | 8/1989 | Duke et al. | 562/401 |
| 4,980,065 | 12/1990 | Hsu | 210/634 |

OTHER PUBLICATIONS

Albertsson, Partition of Cell Particles and Macromolecules (Wiley, 1986).
Albertsson, Particle Fractionation in Liquid Two-Phase Systems, Biochemicia et Biophysical ACTA vol. 27 (1958).

*Primary Examiner*—W. Gary Jones
*Attorney, Agent, or Firm*—Oblon, Spivak, McClelland, Maier & Neustadt

[57] ABSTRACT

An organic two-phase system useful for the separation and purification of chemicals, biochemicals and optical isomers. The two-phase system can be formed with water soluble polymers as one phase, and chiral compound as the other phase together with a water-miscible organic solvent and/or water.

38 Claims, No Drawings

SEPARATION OF MIXTURES BY TWO-PHASE SYSTEMS

This is a continuation-in-part of U.S. Ser. No. 423,333 filed Oct. 18, 1989, now U.S. Pat. No. 4,980,065.

BACKGROUND OF THE INVENTION

1. Field of the Invention

This invention is directed to a method of separation and extraction of organic compounds, inorganic compounds, biomolecules and biomaterials by partition using aqueous two-phase solvent systems or organic two-phase solvent systems.

2. Discussion of the Background

The separation of a mixture by distribution between two immiscible liquids, either by bulk extraction or by liquid-liquid partition chromatography is known. Especially well known in this regard are systems containing an immiscible organic solvent and water. These systems are especially useful for mixtures that contain both a water-soluble and a water insoluble component.

Also, advantage has been taken of the phase separation that frequently occurs when aqueous solutions of two structurally different water-soluble polymers are mixed at or above critical concentrations. These systems separate into two immiscible water-containing liquid phases, each phase enriched with respect to one of the polymers. Such aqueous two-phase systems are suitable for separation of labile materials such as enzymes, cells and organelles.

Aqueous two-phase systems containing two polymers, most commonly polyethylene glycol (PEG) and dextran have found wide application for the separation of biological materials. The phases have low osmotic pressure and high water content. Salts and other solutes can be included to provide buffering capacity. Systems containing a single polymer and a high concentration of some particular salt, e.g., polyethylene glycol (PEG) and a phosphate, have also proven useful in the separation of macromolecules. However, these systems have not been suitable for the separation of optical isomer mixtures or organic molecules which have low solubility in water. A description of two-polymer systems and polymer-salt systems as applied to separation of biological materials can be found in Walter, H. et al, "Partitioning in Aqueous Two-Phase Systems" (Academic Press, 1985) and Albertsson, p. "Partition of Cell Particles and Macromolecules" (Wiley, 1986).

Existing methods to separate optical isomers are based on chromatographic techniques, selective enzymatic reactions, and fractional crystallization of diastereomeric complexes formed with chiral resolving agents. The most common technique used on an industrial scale is fractional crystallization. For example Manghisi et al, U.S. Pat. No. 4,533,748 teaches the use of L-lysine to form diastereomeric salts with a racemic propionic acid derivative followed by fractional crystallization. Fahnenstich et al, U.S. Pat. No. 3,980,665, discloses the use of L-lysine to convert D,L-penicillamine to D-penicillamine. Chibata et al, U.S. Pat. No. 4,519,955, discloses a method of optical resolution of α-amino acids and α-phenylethane sulfonic acids by fractional crystallization. Optical resolution of a D,L-amino acid is disclosed in Yukawa et al, U.S. Pat. No. 4,610,820, which comprises reacting the mixture with an optically active N-acylaspartic acid, followed by fractional crystallization.

A method to resolve stereoisomers that relies on a two-phase water-organic solvent system is disclosed by Empie, U.S. Pat. No. 4,636,470. The method relies upon the preferential enzymatic hydrolysis of one enantiomer of D,L-phenylalanine. The racemate is dissolved in a substantially water immissible organic material which is a solvent for the amino acid racemate but not for the resolved amino acid.

McCloud (Dissertation Abstract B 1969, 29 (7), 2357-8) discloses the resolution of D,L-camphoric acid, D,L-dibromobutanediol, and D,L-isohydrobenzolin isomers by solvent extraction using water and D-tartrate esters as solvents in a two-phase system.

A method of separation of optical isomers based on stereospecific interactions with asymmetric sorbents and solvents was disclosed by Buss et al, Ind. Eng. Chem., V60 (8), p. 12–28, 1968, however asymmetric solvents are prohibitively expensive. The extensive reviews of chiral adsorbents for analytical separation of optical isomers can be found in Lough, W. J. et al, "Chiral Liquid Chromatography" (Blackie and Son, 1989) and Allenmark, S. G., "Chromatographic Enantioseparation: methods and Applications" (Ellis Horwood Limited, 1988).

These methods to separate optical isomers are expensive and require several steps. They are highly specialized procedures which must be developed specifically for the optical isomer mixture to be resolved. For example, conditions which effect the selective crystallization of a diastereomeric mixture must be carefully controlled with respect to concentration and mass transfer effects. In addition, these systems often do not yield the high purity product one desires.

Therefore a need still exists for inexpensive and generally applicable methods for separating stereoisomers and biomolecules especially as applied to industrial processes.

SUMMARY OF THE INVENTION

Accordingly, it is an object of this invention to provide a novel process for the facile and efficient separation of stereoisomers of organic and inorganic compounds.

It is another object of this invention to provide an improved process for the separation of organic and inorganic compounds, and biomaterials such as peptides, proteins, cells and cell particles.

Another object of this invention is to provide an improved process for affinity partitioning and for partition affinity ligand assays.

Another object is to provide novel aqueous two-phase systems and novel organic two-phase systems that can be used for analytical, preparative and large scale commercial separations in combination with known methods such as partition chromatography, counter-current distribution, cross-current extraction and countercurrent extraction.

These and other objects which will become apparent from the following description have been achieved by the present invention which is discussed in detail below.

DETAILED DESCRIPTION OF THE PREFERRED EMBODIMENTS

In the present invention, separation of mixtures including the resolution of stereoisomers is achieved by partition between two phases of an aqueous two-phase system or an organic two-phase system comprising a) a water soluble polymer, b) water and/or a water-miscible organic solvent, c) a previously undisclosed group of phase-forming compounds which cause the separation of the system into two immiscible liquid phases; and d) the mixture to be separated. Soluble and insoluble materials added to these systems distribute themselves between the bulk phases and the interphase. In the case of the separation of racemic mixtures, component (c) may act as a chiral resolving agent.

The water-miscible organic solvent in both phases is the same organic solvent, such as dimethylsulfoxide, formamide, or ethanolamine. Throughout this disclosure "Water-miscible organic solvent" is defined as a solvent which has the solubility of at least 50%, by weight, in water. The organic solvent can be replaced in part or in total by water, resulting in an aqueous two-phase system.

It has been discovered that a solution containing a water-soluble polymer plus an amino acid, protein, peptide, monosaccharide, disaccharide, cyclodextrin, or chiral compound surprisingly will form aqueous or organic two-phase systems. These systems are capable of resolving mixtures of optical isomers such as other amino acids, for example. These novel two-phase systems are also capable of separating cell particulates, such as mitochondria, chloroplasts, membranes, liposomes, chromosomes; macromolecules such as proteins, nucleic acids and water soluble polymers; cells such as bacteria, fungi, algae, erythrocytes, lymphocytes, leukocytes and cancer cells; organic and inorganic compounds, such as metals recovery, actinides and lanthanides from nuclear wastes, organic pollutants from waste water, and americium and plutonium recovery from nitric acid waste streams.

Mixtures of amino acids, alcohols, amines, halides, bases, acids, aldehydes, ketones, fats; amides, peptides, carbohydrates, etc., containing chiral atoms will interact with the chiral resolving agent thereby forming diastereomeric complexes. If the chiral material is a mixture, e.g., a racemic mixture, differential partitioning of the diastereomeric complexes occurs between the phases.

It has been found that monosaccharides, disaccharides, cyclodextrins, peptides, proteins, antibodies, optically active amino acids and their derivatives can fulfill the requirements of the phase-forming agent (c) described above. Optically active salts, acids, bases, esters and solvents can also act as a chiral resolving agent in (c).

Suitable amino acids include the D- or L- naturally occurring α-amino acids, such as alanine, lysine, serine, proline, etc., as well as other chiral amino acids. By "chiral amino acids" is meant any amino acid which is substantially soluble in water-miscible organic solvents or water and which contains at least one chiral carbon atom. Chiral amino acids include the natural and non-natural amino acids generally having fewer than 50 carbon atoms and, preferably fewer than 20 carbon atoms. The chiral amino acids may be substituted with one or more functional groups such as hydroxy, carboxylic acid, amino, substituted amino, thiol groups, and other derivatives, etc., to enhance solubility and chirality of the compound.

Although glycine is not a chiral amino acid, it and its derivatives can form the aqueous or organic two-phase systems of the present invention to be used for the separation of organic compounds, inorganic compounds, biomolecules and biomaterials. A chiral additive selected from the group of amino acids, peptides, proteins, monosaccarides, disaccarides, cyclodextrins, antibodies, chiral salts, chiral acids, chiral bases, chiral esters and chiral solvents as described in this invention can modify the polymer/glycine/water or polymer/glycine/water-miscible organic solvent systems to effect resolution of stereoisomers. In addition, glycine can be modified to result in a chiral compound.

It has been discovered that monosaccharides and disaccharides, most of which are optically active compounds, can also function as the phase-forming agent. These sugars can form aqueous or organic two-phase systems with polyethylene glycol, polypropylene glycol and other water soluble polymers. The phase forming monosaccharides and disaccharides include arabinose, glucose, galactose, dextrose d-glucose, fructose, lactose, levulose, maltose, mannose, xylose, sucrose and others. The natural alditols, inositols, aldonic acids, uronic acids, aldaric acids, monosaccharides and disaccharides described in Weast, R. C., "Handbook of Chemistry and Physics," The Chemical Rubber Co. (CRC), Cleveland, Ohio, 63rd edition, b 1982, C-760 to C-767; and Davidson, E. A., "Carbohydrate Chemistry," Holt, New York, 1967, as well as the derivatives of these compounds are within the scope of the present invention.

Cyclodextrins are chiral, toroidal-shaped molecules formed by the action of the enzyme cyclodextrin transglycosylase on starch. These cyclic oligomers contain from 6 to 12 glucose units bonded through α-(1,4)-linkages. The three smallest homologs, α-cyclodextrin, β-cyclodextrin and γ-cyclodextrin are available commercially, while larger homologs must be produced and isolated individually. The secondary 2- and 3-hydroxyl groups line the mouth of the cyclodextrin cavity and have a staggered orientation. The primary 6-hydroxyls are at the opposite end of the molecule. The inside of the cyclodextrin cavity is relatively hydrophobic since all hydroxyls are directed toward the outside of the molecule. Cyclodextrins are known to form inclusion complexes with a variety of guest molecules, i.e. molecules which are taken up by the host molecule, cyclodextrin. It has been discovered that the cyclodextrins and their derivatives can also function as phase-forming agents. These cyclodextrins and their derivatives can form aqueous and organic two-phase systems with polyethylene glycol, polypropylene glycol and other water soluble polymers. The cyclodextrin/polymer/water systems and the cyclodextrin/polymer/water-miscible organic solvent systems can separate organic compounds, inorganic compounds, biomolecules, biomaterials and optical isomers.

Optically active salts, acids, bases, esters and water miscible solvents as well as their derivatives are also phase forming agents when added to the aqueous or organic solution which contains water soluble polymers. Examples include lead hydrosulfate, potassium hydrosulfate, amyl alcohol, camphor, cedar oil, citrol oil, ethyl malate, menthol, bromocamphorsulfonic acid, camphorsulfonic acid, chlorocamphorsulfonic acid, codeine sulfonic acid, hydroxybutyric acid, lactic acid, malic acid, mandelic acid, methylene-camphor, phenylsuccinic acid, tartaric acid, brucine, cinchonidine, cinchonine, cocaine, coniine, codeine, hydrostine, menthylamine, narcotine, quinidine, quinine, thebaine, strychnine, potassium tartrate, quinine sulfate, santonin, sodium potassium tartrate, terpenes, tartaric acid, ascorbic acid and their derivatives.

The optically active salts, acids, bases, esters and water miscible solvents described in Weast, R. C., "Handbook of Chemistry and Physics," The Chemical Rubber Co. (CRC), Cleveland, Ohio, 63rd edition, 1982, E404-406, as well as their derivatives, are considered to be Within the scope of the present invention.

Proteins, peptides and antibodies which can be used both as the phase-forming component and as the chiral resolving agent include peptides as small as dipeptides and include proteins having up to 1,000,000 amino acid residues, as long as the peptide has substantial solubility in water or a water miscible solvent. Amino acid homopolymers such as polylysine, polyglycine, etc. are also included as suitable peptides. Preferred peptides and proteins are those having from 2-1000,000 amino acid residues with peptides and proteins having 2-1000 amino acid residues being particularly preferred. Specific examples of suitable peptides and proteins which may be used as the chiral resolving agent include trypsin, chymotrypsin, pepsin, lipase, cytochrome c, ribonuclease, lysozyme, myoglobin, rhodanese, ovalbumin, amylase, protease, transferrin, conalbumin, bovine serum albumin and thyroglobulin.

Polymers which are useful for the preparation of aqueous and organic two-phase systems include both synthetic polymers and purified natural polymers. Any water soluble polymer capable of forming a two-phase system with an organic solution of component (c), above, as well as their derivatives, is within scope of the invention. In general these polymers have a molecular weight in the range of 200-50,000, preferably 200-35,000. Preferred polymers are water soluble polymers based on sugars and polyalkylene glycols prepared from glycols having 2-8 carbon atoms based on hydrocarbon ether units.

The polymers may also be derivatized to provide additional solubility in water or organic solvents and chirality for the system and to adjust the separation factor as discussed below. Suitable derivatives are amino, alkylamino, carboxyl, aldehyde, ketone, amine, amide and carbohydrated derivatives, for example PEG - fatty acid esters and diethyleneaminoethyl-dextran.

Examples of commercially available sugar polymers include the glucose polymer dextran, polysucrose, pullulan, methyl cellulose, ethylhydroxyethylcellulose, hydroxypropyldextran, ficoll, sodium dextran sulfate, butylcellosolve, sodium carboxymethyldextran, sodium carboxymethylcellulose, DEAE dextran-HCl, starch and other polysaccharides.

Commercially available hydrocarbon ether polymers include polyethylene glycol (PEG) of different molecular weights, polypropylene glycol, methoxypolyethylene glycol, polyvinyl alcohol and polyethylene glycol-polypropylene glycol copolymers. Polymers prepared from hydrocarbon, aromatic, aliphatic and cycloaliphatic amines such as polyvinylpyrrolidone are also suitable.

PEG is a linear synthetic polymer available in a variety of molecular-weights. PEG is quite stable in solution, in the dry powdered or flake form in which it is sold. Common fractions of PEG supplied by Union Carbide Corporation used in the present phase partitioning process include PEGs having a molecular weight in the range of about 200-50,000 preferably the range 200-35,000 such as PEG 200, PEG 300, PEG 400, PEG 3,400, PEG 8,000 and PEG 20,000. Other commercial names for PEGs include polyglycol E (Dow Chemical), carbowax (Union Carbide), and pouracol E (BASF) (Wyandotte Corp).

Dextran, predominantly poly($\alpha$-1,6 glucose) is commercially available in a range of molecular weight fractions from approximately 2,000 to 2 million. Similar molecular weights of derivatives are also useful.

Added salts, such as potassium phosphate, sodium chloride, ammonium sulfate, magnesium sulfate, copper sulfate, sodium sulfate and lithium sulfate, optically active salts (as described above), amino acids, monosaccharides and disaccharides (as described above), cyclodextrins, peptides and proteins which are added to the water soluble polymer (a) to enhance the solubility, phase separation, separation factor, or chirality are also considered to be within the scope of the present invention.

Stock solutions of the polymers are formed using known methods such as described in Walter et al. and Albertsson.

Stock solutions of dextran of 20-30% by weight are made by mixing the powder into a paste with an equal weight of organic solvent or water, then adding enough solvent by weight to yield an apparent concentration approximately 10% higher than desired in order to allow for water or organic solvent in the dextran. Dextran stock solutions are stirred 2-3 hours at room temperature, but the time may be shortened with heating. Concentrations of dextran stock solution can be determined by polarimetry.

PEG stock solutions of 30-40% by weight are made up by accurate weighing of the powder and dissolution in water or organic solvent at room temperature. PEG dissolves readily in water or organic solvent on stirring for a couple of hours and fresh, properly stored PEG powder usually contains less than 0.5% water. The stock concentration can be measured by refractive index.

Preferably, stock solutions of amino acids, salt, sucrose, etc. are made up at least four times the concentration by weight desired in the phase system.

The biphasic systems can also be prepared by weighing appropriate quantities of PEG (in solid-form), amino acid stock solution, and solvent into a beaker. Thirty grams of a system may be easily prepared. The resulting solution is magnetically stirred for 3 hours, after which it is poured into a centrifuge tube. The phase systems are allowed to equilibrate at 5 min. to 24 hours depending on the system.

The aqueous or organic two-phase system may be prepared from the stock solutions of polymer and concentrated phase-forming compound solutions. The stock solutions may contain known buffers to control the pH and salts to increase the tonicity of the solutions. Preferably, potassium phosphate buffer is used to adjust the pH. These buffers and salts are selected according to the nature of the material to be separated and can be readily determined by one skilled in the-art using the criteria set forth below. For example, since the water soluble polymers are generally ion-free and have large molecular weights, their contribution, at high concentrations, to the tonicity of a solution is small. If a mixture to be separated comprises a protein which would be denatured by low ionic strength solutions, the addition of salts would be indicated. The tonicity of the phases can be measured by using a vapor pressure osmometer.

Additives such as salts, buffers, sugars and polymers may be added to enhance phase separation and separation factor. Suitable additives include potassium phosphate, glucose, glycerol, butylcellusolve, propylalcohol and sodium chloride. Additives which can increase the difference in density or hydrophobicity between the two phases, reduce the viscosities of either phase, or increase the interfacial tension between the two phases, will enhance phase separation and separation factor.

The temperature and pressure can also be manipulated to enhance phase separation and partition coefficient. Suitable temperatures span the range from where the liquid two-phase system begins to freeze up to the boiling point of the solvents, in general from about $-10°$ C. to $140°$ C. The preferred temperature is from $-10°$ C. to $80°$ C. temperature. The range of pressure includes all pressures which result in a two-phase system, in general from 0.01 to 1,000 atmospheres. The preferred pressure is ambient pressure.

The two-phase system is generally prepared from the stock solutions. The amount of the chiral compound in the two-phase system is generally in the range of about 0.01-1.00.0 wt.% relative to the weight of the aqueous or organic two-phase system. Preferably, the chiral compound is present in an amount of about 0.1-70 wt.%. In general, the water soluble polymers are present in amounts from about 2-100 wt.%, preferably 2-70 wt.% relative to the weight of the two-phase system, with the balance being water and/or organic solvent. Obviously, amounts of chiral compound and water soluble polymer may vary above or below these numerical ranges so long as a two-phase system is produced when the stock solutions of chiral compound and water soluble polymer are mixed. All proportions of chiral compound and water soluble polymer which interact to form an aqueous or organic two-phase system are considered to be within the scope of the present invention.

In order to separate two components of a mixture in one or only a few steps, the partition behavior of the components must be manipulated in a manner such that one component is in one phase and the other component is in the other phase or at the interphase. Using the present method, D,L-amino acids can be separated into two fractions each partially enriched with one optical isomer. The separation factor ($\alpha = K_A/K_B$), is defined as the ratio of partition coefficient $K_A$ of component A to partition coefficient $K_B$ of component B. The partition coefficient is defined as the ratio of the concentration in the upper phase to that of bottom phase. The separation factor can be any value other than 1.0, and is preferably less than 0.98 or larger than 1.02. When $\alpha = 1.0$, A and B will not be able to be resolved.

For mixtures that do not differ greatly in their partitioning behavior, i.e., a separation factor close to b 1.0, single extraction steps are not sufficient to produce a separation. In such cases multiple extraction procedures such as countercurrent distribution (CCD), thin-layer counter-current distribution, enhanced gravity countercurrent distribution, partition column chromatography, countercurrent chromatography, liquid-liquid extractors, centrifugal liquid-liquid extractors, multi-stage cross-current extractors and counter-current extractors are required. The preferred methods are CCD and counter-current partition chromatography, which perform a discrete number of partition steps with thin layers or small chamber of each phase. Continuous cross-current and counter-current extraction methods using columns are preferred methods. The theory of CCD and the design and use of the thin-layer CCD apparatus are described by Walter et al. The theory and practice of cross-current and counter-current extraction are described by Treybal, R., "Liquid Extraction" McGraw Hill, 1963.

The extraction procedures can also be performed in a membrane-mediated extractor. In this extractor one of the phases of the two-phase system can be fed into the bore side of a microporous membrane. The membrane can be a hollow fiber module. The other phase will be fed into the shell side of the microporous membrane. Both phases can run in the membrane unit as concurrent or counter-current extractor.

Immobilizing the phase-forming agents of one phase on solid supports via chemical covalent bond linkage, or chemical and physical adsorption, and to be used as partition chromatography, is considered to be within the scope of the present invention.

Separation with the two-phase systems of the present invention depends on the choice of phase composition so as to obtain appropriate partition coefficients for the materials of interest. There are four major ways in which these systems can be manipulated or adjusted so as to give phases with appreciably different physical properties: 1) choice of polymer, polymer concentration, polymer molecular weight; 2) choice of the phase forming agent, e.g., monosaccharide, disaccharide, cyclodextrin, chiral compound, chiral amino acid, peptide or protein and its concentration; 3) chemical modification of the water soluble polymer by derivatization or by attaching a ligand for which receptors exist on the material of interest resulting in a procedure called affinity partitioning; 4) and choice of water and/or organic solvent.

With regard to the choice of the water soluble polymer we prefer the polymer which gives a higher density difference from the chiral phase, lower viscosity, higher interfacial tension between the two phases, lower concentration to form two phases and lower toxicity.

With regard to the phase-forming chiral agent we prefer the compound which gives higher specific rotation $[\alpha]^{25}_D$, (definition of specific rotation is provided in Lehninger, A. L., "Biochemistry", Worth Publishers, 1975, page 81) higher density difference from the other phase, lower viscosity, lower concentration to form two phases, less toxicity and higher interfacial tension between the two phases. Besides chiral amino acids, peptides and proteins, chiral compounds, such as monosaccharides and disaccharides, cyclodextrins, chiral salts, chiral solvents, chiral esters, chiral acids and chiral bases also are considered to be within the scope of the present invention.

Another embodiment of the invention is in the modification of known, non-chiral, aqueous two-phase systems. The chiral phase-forming component (component c, above) of the present invention may be added to an already formed aqueous two-phase system which comprises PEG-phosphate salt-water, PEG-dextran-water or POLYx-POLYy-water, where POLYx and POLYy represent different polymers, to obtain the two-phase systems with chirality of the present invention. Also, a portion or all of the water can be replaced with a water-miscible organic solvent such as dimethylsulfoxide resulting in the organic two-phase systems of the present invention.

The method of the present invention may also be used for affinity partitioning. When an affinity interaction takes place between a target molecule to be separated and an affinity agent or ligand (for example an antibody) in free solution, a soluble complex is formed. The partition behavior of this complex is dependent upon the characteristics of the individual components. In an ideal situation an affinity agent such as an antibody favours one phase to such an extent that the antibody-target molecule complex will also partition to the same phase. The aqueous and organic two-phase systems with chiral phase-forming components of the present invention have been found to meet the requirements of an affinity partition system very well. By utilizing the affinity partitioning concept, one can manipulate the separation factor (or partition coefficient) of target molecules by immobilizing an affinity agent on one of the phase components, the polymeric or the chiral one, to enhance separation.

Affinity partitioning is based upon the principle that the complex should have a different partition pattern as compared to the free target molecule. When the affinity agent or ligand does not exhibit extreme partition behavior, it must be chemically modified prior to use. In most cases, chemical compounds partition into the bottom phase and the desire has therefore been to selectively transfer the target molecule to the top phase. To make the affinity agent favor the top phase, chemical coupling of the affinity agent to the top phase polymer has been used. Since poly(ethylene glycol) is the major top phase polymer used, this has meant coupling of PEG to the affinity agent. A large number of coupling reactions have been applied to PEG and today there are several alternatives available (Harris, J. M., Review in Macromol. Chem. and Phys., C25, 325-373 (1985)).

The affinity partitioning takes place as follows: The modified ligand is mixed with the mixtures and after proper binding has taken place the phase system is added. After proper mixing, phase separation takes place and the affinity complex is then found in the top phase. A normal procedure for isolating a pure target molecule freed of affinity agent or ligand and phase components has involved the use of a second partition step wherein the top phase has been mixed with a fresh bottom phase under dissociating conditions. During mixing of the phases, dissociation of the complex takes place and the target protein will then parititon according to the spontaneous pattern, i.e., it will be recovered from the bottom phase. Isolation of the target molecule from the phase components may be done using ion exchange chromatography or membrane filtration. The ligand may be recovered from the top phase and reused.

Affinity partitioning as described above involves the need of modifying each individual inhibitor or ligand to go to the top phase. This may be impractical and in some cases even unsuitable. Therefore, the strategy of applying a second separator molecule having an affinity for the ligand - target protein complex and a partition behavior strongly favoring the top phase has been developed. An example of this is the protein avidin that was PEG-modified, and the ligand was modified with biotin residues in a mild and gentle modification reaction. A similar approach was applied in immunoaffinity partitioning by applying protein A or G as the separator molecule to be modified for extreme partitioning. As stated above, even if soluble molecules may be partitioned to one phase, it is much easier and more predictable to use particles. Therefore, second separator particles were developed as well. The same approach to modify the chiral resolving agent (c) for affinity partitioning is considered to be within the scope of the present invention.

Partition affinity ligand assay is described by Mattiasson, B. and Ling, T. G. I., J. Immunol. Meth. 38, 217-223 (1980), and Mattiasson, B. in "Separations for Biotechnology" ed. by Verrall, M. S. and Hudson, M. J., Ellis Horwood, page 281-283, (1987). Binding assays involve the formation of affinity complexes. The dominating problem in conventional immunological assays is to carry out separation of bound antigen from free antigen in an efficient, quick, and reproducible way. The separation principle of water-soluble polymer/chiral agent/aqueous and/or organic solvent two-phase systems meets these demands very well and is considered to be within the scope of the present invention. Also, in these applications there may also be a need for modifying one of the reactants.

The method of the present invention is also useful for extractive biocatalytic conversions. When used for such purposes, the components of the bioconversion system, for example, enzymes plus the required buffers, cofactors, etc., are mixed into the organic or aqueous two-phase system. Upon addition of the appropriate substrate for the enzyme or enzyme system, bioconversion is effected and product compounds are produced by the biocatalytic or enzyme system. When the enzyme system is preferably soluble in the lower phase of the two-phase system and the product produced by bioconversion is preferably soluble in the upper phase of the two-phase system, a continuous extraction process is established in which the product obtained by bioconversion in the lower phase is continuously extracted into the upper phase by means of the aqueous or organic two-phase system of the present invention. Product feedback inhibition of the enzyme system is substantially reduced since the product is continuously extracted away from the components of the bioconversion system. Obviously, extractive bioconversions may be performed when the components of the bioconversion system are present in either phase of the two-phase system so long as the product produced is soluble in the opposite phase.

The present method of separating a mixture of organic compounds, inorganic compounds, biomolecules and biomaterials is flexible and inexpensive. The method may be applied to the separation of a wide variety of biological materials and is particularly interesting for the separation of stereoisomers. The organic two-phase systems are most useful for the separation of water-insoluble organic compounds. The method is also generally useful in the areas of extractive bioconversions and affinity partitioning.

Other features of this invention will become apparent in the course of the following description of exemplary embodiments which are given for illustration of the invention and are not intended to be limiting thereof.

EXAMPLES

Example 1

Aqueous two-phase systems containing chiral amino acid-water soluble polymer-water are prepared as follows:

An appropriate quantity of distilled water is weighed in a beaker. Add an appropriate quantity of either amino acid, monosaccharide, disaccharide, or chiral compound, to the water, which is stirred and dissolved. With the water still being stirred, add an appropriate quantity of water soluble polymer. Continue stirring until the polymer dissolves. Stop mixing and let the system settle into two phases.

The following compositions of chiral amino acid/water-soluble polymer/water form aqueous two-phase systems:

a) 23.08% L-lysine/5.77% PEG-20,000/71.15% water at 25° C.
b) 33.33% L-proline/5.00% PEG-20,000/61.67% water at 25° C.
c) 13.04% L-alanine/6.50% p-EG-20,000/80.37% water at 51.5° C.
d) 9.78% L-proline/51.10%PPG-425/39.12% water at 25° C.

Example 2

Aqueous two-phase systems containing monosaccharides or disaccharides/water soluble polymer/water were prepared based on the same procedure described in Example 1.

The following are compositions of monosaccharides or disaccharides/water soluble polymer/water that form aqueous two-phase systems:

a) 29.40% glucose/29.40% PPG-425/41.20% water at 25° C.
b) 30.00% fructose/15.00% PPG-425/55.00% water at 25° C.
c) 25.72% fructose/27.14% PPG-425/47.14% water at 25° C.
d) 30.00% maltose/30.00% PPG-425/40.00% water at 25° C.
e) 41.20% sucrose/24.15% PPG-425/34,65% water at 25° C.
f) 44.44% sucrose/5.56% PEG-20,000/50/50.00% water at 73° C.

Example 3

Aqueous two-phase systems containing chiral compounds or salts-water soluble polymer/water were prepared based on the procedure described in Example 1.

The following are compositions of chiral acid or salt/water soluble polymer/water that form aqueous two-phase systems:

a) 16.04% L-ascorbic acid and 8.53% NaOH/8.21% PEG-8000/67.22% water at 25° C.
b) 6.67% L-sodium tartrate/16.67% PEG-8000/66.66% water at 25° C.

Example 4

D and L phenylalanine separation:

The following L-lysine/PEG8000/H$_2$O system was prepared at 25° C.: 28.57% w/w L-lysine, 10.71% w/w PEG8000, 60.72% w/w water. 10 ml of the phase system was poured into 15ml, polypropylene centrifuge tubes. 6mg of L-phenylalanine was added to one tube, 6mg of D-phenylalanine to a second, while the third tube was left blank. The contents of the tubes were mixed, and then permitted to settle over a period of time. The partition coefficients were determined by diluting the phases 1/5 and measuring absorbance at 254 nm versus an appropriately diluted phase blank. The results of three different tests were as follows:

|  | Partition Coefficient, K | | |
| --- | --- | --- | --- |
|  | Sample 1 | Sample 2 | Sample 3 |
| L-Phenylalanine | 0.979 | 0.974 | 0.968 |
| D-Phenylalanine | 1.094 | 1.061 | 1.053 |
| Separation Factor ($\alpha = K_D/K_L$) | 1.11 | 1.09 | 1.09 |

L-phenylalanine gives a lower partition coefficient than D-phenylalanine and is, therefore, enriched in the L-lysine (lower) phase.

Example 5

β-lactoglobulins A and B separation:

β-lactoglobulin concentration was 1.0 mg/ml, and 10 ml of two-phase system with composition of 28.57% L-lysine, 10.71% PEG 8000 and 60.72% water was utilized. The separation factor ($\alpha$) is 1.94 in favor of β-lactoglobulins A in upper phase.

Example 6

D and L tryptophan separation:

D and L tryptophan were partitioned in the aqueous two-phase system with composition of 28.57% L-lysine, 10.71% PEG 8000 and 60.72% water. The separation factor $\alpha$ is 1.24 in favor of D-tryptophan in the upper phase.

Example 7

D and L tryptophan separation:

D and L tryptophan were partitioned in the aqueous two-phase system with composition of 14.60% L-serine, 11.00% PEG 20,000 and 74.4% water. The separation factor $\alpha$ is 1.19 in favor of D-tryptophan in the upper phase.

Example 8

D and L tryptoph separation:

D and L tryptophan were partitioned in the aqueous two-phase system with composition of 36.59% L-proline, 9.76% PEG 8000 and 53.65% water. The separation factor $\alpha = 1.06$ in favor of D-tryptophan in the upper phase.

Example 9

D and L tryptophan separation:

D and L tryptophan were partitioned in the aqueous two-phase system with composition of 36.59% L-proline, 9.76% PEG 8000, 53.65% water and 0.008 M copper sulfate at 22° C. The separation factor $\alpha = b$ 1.18 in favor of D-tryptophan in the upper phase.

Example 10

D and L tryptophan separation in PPG/Sucrose/H$_2$O aqueous two-phase system;

D and L tryptophan were partitioned in the aqueous two-phase system with composition of 41.20% sucrose, 24.15% polypropylene glycol-425, 34.65% water. The separation factor $\alpha = 0.90$ in favor of D-tryptophan in the lower (sucrose) phase.

Example 11

D and L tryptophan separation in PEG/Potassium phosphate/L-lysine/water system;

Stock solutions composed of 9.42% polyethylene glycol/11.37% potassium phosphate/79.21% water were prepared. 20 gm of top and bottom phase was weighed into a 100ml beaker. 10 gm L-lysine was then added, and stirred until the lysine dissolved. 10 ml of the phase system was then poured into each of three polypropylene centrifuge tubes. 3 mg of D-tryptophan was added to the first tube, 3mg of L-tryptophan was added to the second, while the third was left blank. After allowing the tryptophan to dissolve, the systems were settled at room temperature. The top and bottom phases were collected and the concentration of either D and L tryptophan were determined by UV spectrophotometer at 280 nm. The separation factor ($K_D/K_L$) was 1.03.

Example 12

(Comparative)

The process of Example 11 was repeated with the omission of L-lysine. The separation factor of the PEG/potassium- phosphate/water system without L-lysine was 1.0.

Example 13

Aqueous two-phase system containing cyclodextrin/water soluble polymer/water was prepared based on the procedure described in Example 1. The composition of the aqueous two-phase system is 20% w/w hydroxyethyl-$\beta$-cyclodextrin/35% w/w PPG-425/45% w/w $H_2O$.

Example 14

D and L tryptophan separation;

D and L tryptophan were partitioned in the aqueous two-phase system of Example 13 with composition of 20% w/w hydroxyethyl-B-cyclocyclodextrin/35% w/w PPG-425/45% w/w $H_2O$—The separation factor is 0.96 in favor of L-tryptophan in the upper phase.

Example 15

(1S, 2R)- and (1R, 2S)- ephedrine separation;

(1S, 2R)- and (1R, 2S) - ephedrine were partitioned in aqueous two-phase system of Example 13 with composition of 20% w/w hydroxyethyl-$\beta$-cyclodextrin/35% w/w PPG-425/45% w/w $H_2O$. The separation factor of (1S, 2R) -ephedrine/(1R,2S)-ephedrine is 1.09.

Example 16

Aqueous two-phase systems containing non-chiral amino acid-water soluble polymer-water was prepared based on the procedure described in Example 1. The composition of the non-chiral amino acid aqueous two-phase system is 12.5% w/w glycine/12.5% w/w PEG-8000/75.0% w/w water.

Example 17

Organic two-phase systems containing chiral compound/polymer/organic solvent are prepared as follows:

An appropriate quantity of organic solvent is weighed in a beaker. Add an appropriate quantity of either amino acid, monosaccharide, disaccharide, polysaccharide, carbohydrate, or chiral compounds, to the organic solvent, which is stirred and dissolved. With the organic solvent still being stirred, add an appropriate quantity of soluble polymer. Continue stirring until the polymer dissolves. Stop mixing and let the system settle into two phases.

The following compositions of chiral carbohydrate or amino acid-polymer-organic solvent form organic two-phase systems at room temperature:

a) 9.05% sucrose/45.47% PPG-425/45.48% dimethyl sulfoxide (DMSO)
b) 15.01% D-fructose/37.90% PPG-425/47.09% DMSO
c) 16.10% D-maltose/32.21% PPG-425/51.69% DMSO
d) 14.84% D-gluconic acid/37.48 PPG-425/47.68% DMSO
e) 9.61% sucrose/48.56 PPG-425/41.83% formamide
f) 16.56% D-mannose/42.03 PPG-425/41.41% formamide
g) 8.81% D-galactose/42.73 PPG-425/48.46% ethanolamine
h) 11.06% D-fructose/44.47 PPG-425/44.47% ethanolamine
i) 20.00% L-proline/30.00% PPG-425/50.00% formamide Example 18

D and L-tryptophan separation:

The following D-fructose/PPG-425/DMSO system was prepared at 25° C.: 15.01% D-fructose/37.90% PPG-425/47.09% DMSO. 10 ml of the phase system was poured into 15 ml polypropylene centrifuge tubes. 6 mg of L-tryptophan was added to one tube, 6 mg of D-tryptophan to a second, while the third tube was left blank. The contents of the tubes were mixed, and then permitted to settle over a period of time. The partition coefficients were determined by diluting the phases 1/5 and measuring absorbance at 254 nm versus an appropriately diluted phase blank. The partition coefficient of L-tryptophan and D-tryptophan is 0.192 ($K_L$) and 0.157 ($K_D$), respectively. The separation factor ($K_L/K_D$) is 1.22. D-tryptophan gives a lower partition coefficient than L-tryptophan and is, therefore, enriched in D-fructose (lower) phase.

Example 19

D and L-tryptophan separation:

D and L tryptophan were partitioned in the organic two-phase system with composition of 16.10% D-maltose/32.21% PPG 425/51.69% DMSO. The separation factor is b 1.20 in favor of D-tryptophan in the lower phase.

Example 20

D and L-tryptophan separation:

D and L tryptophan were partitioned in the organic two-phase system with composition of 20% L-Sorbose/30.0% PPG-425/50.00% DMSO. The separation factor is 0.78 in favor of D-tryptophan in the upper phase.

Example 21

(1S, 2R)- and (1R, 2S)-ephedrine separation:

(1S, 2R)- and (1R, 2S)-ephedrine were partitioned in the organic two-phase system with composition of 20.0% glucose/30.0% PPG-425/50.0% DMSO. The separation factor of (1S, 2R)-ephedrine/(1R, 2S)-ephedrine is 0.88.

Example 22

((1R, 2R)- and (1R, 2S)-norephedrine separation:

(1S, 2R)- and (1R, 2S)-norephedrine wre partitioned in the organic two-phase system with composition of 20% glucose/30% PPG-425/50% DMSO. The separation factor of (1S, 2R)-norephedrine/(1R, 2S) norephedrine is 1.09.

Example 23

(1S, 2R)- and (1R, 2S)-norephedrine separation:

(1S, 2R)- and (1R, 2S)- norephedrine were partitioned in the organic two-phase system with composition of 15.0% L-proline/40.0% PPG-425.0% formamide. The separation factor of (1S, 2R)-norephedrine/(1R, 2S)-norephedrine is 1.06.

Obviously, numerous modification and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for separating a mixture of organic compounds, inorganic compounds, biomolecules and biomaterials, comprising the steps:
    a) preparing an organic two-phase system containing a substantial proportion of organic solvent in both phases consisting essentially of 1) a phase forming compound selected from the group consisting of amino acids, peptides, proteins, alditols, inositols, aldonic acids, uronic acids, aldaric acids, monosaccharides, disaccharides, cyclodextrins, chiral salts, chiral solvents, chiral acids, chiral bases and chiral esters 2) a water soluble polymer in amounts sufficient to form said two-phase system and 3) a water-miscible organic solvent selected from the group consisting of dimethylsulfoxide, formamide and ethanolamine;
    b) mixing said two-phase system with said mixture to be separated;
    c) separating the two phases from each other.

2. The process of claim 1, wherein said phase-forming compound is a D- or L-α-amino acid, glycine, monosaccharaide, disaccharide, cyclodextrin, chiral salt, chiral water miscible solvent, chiral acid, chiral base or chiral ester.

3. The process of claim 1, wherein said water soluble polymer is selected from the group consisting of polyethylene glycol, polypropylene glycol, polyvinyl pyrrolidine, polyvinyl alcohol, dextran and sodium dextran sulfate, each having a molecular weight in the range 200-50,000.

4. The process of claim 3, wherein said polyethylene glycol, polypropylene glycol, polyvinyl pyrrolidone, polyvinyl alcohol, dextran and sodium dextran sulfate each have a molecular weight in the range of 200-35,000.

5. The process of claim 1, wherein said mixture is a mixture of D- and L- amino acids or other optical isomers.

6. The process of claim 1, wherein said mixture is a mixture of cell particulates, macromolecules, cells, chemical or biochemical compounds.

7. The process of claim 1, wherein said phase-forming compound is a peptide having 2-1,000,000 amino acid residues.

8. The process of claim 1, wherein said two-phase system further consists essentially of a water-miscible organic solvent and water.

9. The process of claim 1, wherein said phase-forming compound is present in an amount of 0.1-100 wt.% relative to said two-phase system.

10. The process of claim 1, wherein said water soluble polymer is present in an amount of about 2-100 wt.% based on said two-phase system.

11. The process of claim 1, wherein said mixing step b) is accomplished in a countercurrent distribution, cross-current extraction, counter-current extraction, liquid partition column chromatography, or counter-current chromatography apparatus.

12. The process of claim 1, wherein said mixing and separation steps accomplish a partition chromatography, wherein one of the phases of the two-phase system is chemically bound or physically adsorbed to a solid support, and used as column material for chromatographic separation.

13. The process of claim 1, wherein an additive salt, buffer, sugar or polymer is present in said two-phase system whereby the separation factor, phase separation or solubility is enhanced, the viscosity of either phase is reduced or the interfacial tension between the two phases is increased.

14. The process of claim 13, wherein said two-phase system further consists essentially of a non-chiral phase-forming agent selected from the group consisting of non-chiral water soluble polymers, salts, acids and bases.

15. The process of claim 1, wherein said two-phase system further consists essentially of an affinity agent coupled to the water soluble polymer or phase-forming compound or other carriers to be used in affinity partitioning.

16. The process of claim 1, wherein said two-phase system further consists essentially of an enzyme or biocatalyst system, a substrate for said enzyme together with buffers and cofactors necessary to effect a biocatalytic reaction.

17. A process for separating a mixture of stereoisomers or optical isomers comprising the steps:
    a) preparing an organic tow-phase system containing a substantial proportion of organic solvent in both phases consisting essentially of 1) a phase-forming chiral resolving agent selected from the group consisting of amino acids, peptides, proteins, alditols, inositols, aldonic acids, uronic acids, aldaric acids, monosaccharids, disaccharides, cyclodextrins, chiral salts, chiral solvents, chiral acids, chiral bases and chiral esters 2) a water soluble polymer in amounts sufficient to form said organic two-phase system and 3) a water-miscible organic solvent selected from the group consisting of dimethylsulfoxide, formamide and ethanolamine;
    b) mixing said two-phase system with the mixture of stereoisomers or optical isomers to be separated;
    c) separating the two phases from each other;
    d) recovering a phase which is enriched in one of said optical isomers.

18. The process of claim 17, wherein said chiral resolving agent is a D- or L-α-amino acid, monsaccharide, disaccharide, cyclodextrin, chiral salt, chiral solvent, chiral acid, chiral base or chiral ester.

19. The process of claim 17, wherein said soluble polymer is selected from the group consisting of polyethylene glycol, polypropylene glycol, polyvinyl pyrrolidone, polyvinyl alcohol, dextran and sodium dextran sulfate, each having molecular weight in the range 200-50,000.

20. The process of claim 17, wherein said water soluble polymer is selected from the group consisting of polyethylene glycol, polypropylene glycol, polyvinyl pyrrolidone, polyvinyl alchohol, dextran and sodium dextran sulfate each having molecular weight in the range 200–35,000.

21. The process of claim 17, wherein said mixture to be separated is a mixture of D- and L- amino acids.

22. The process of claim 17, wherein said chiral resolving agent is a peptide having 2–1,000,000 amino acid residues.

23. The process of claim 17, Wherein said two-phase system further consists essentially of a water-soluble organic solvent and water.

24. The process of claim 17, wherein said chiral compound is present in an amount of 0.1–100 wt.% relative to said two-phase system.

25. The process of claim 17, wherein said water soluble polymer is present in an amount of about 2–100 wt.% based on said two-phase system.

26. The process of claim 17, wherein said mixing step b) is accomplished in a countercurrent distribution, cross-current extraction, counter-current extraction, liquid partition column chromatography or counter-current chromatography apparatus.

27. The process of claim 17, wherein said mixing and separation steps accomplish a partition chromatography, wherein one of the phases of the two-phase system can be chemically bound or physically adsorbed to a solid support, and used as column material for chromatography separation.

28. The process of claim 17, wherein an additive salt, buffer, sugar or polymer is present in said two-phase system whereby the separation factor, phase separation or solubility is enhanced, the viscosity of either phase is reduced or the interfacial tension between the two-phases is increased.

29. The process of claim 28, wherein said two-phase system further consists essentially of a non-chiral phase-forming agent selected from the group consisting of non-chiral water soluble polymers, salts, acids, bases and esters.

30. The process of claim 17, wherein said two-phase system further consists essentially of an affinity agent coupled to the water soluble polymer or phase-forming chiral compound or other carriers to be used in affinity partitioning.

31. The process of claim 17, wherein said two-phase system further consists essentially of an enzyme or biocatalyst system, a substrate for said enzyme together with buffers and cofactors necessary to effect a biocatalytic reaction.

32. The process of claim 17, wherein said mixture is a mixture of optical isomers.

33. A process for separating a mixture of organic compounds, inorganic compounds, biomolecules and biomaterials, comprising the steps:
   a) preparing a two-phase system containing a substantial proportion of organic solvent in both phases consisting essentially of 1) a phase forming compound selected from the group consisting of glycine, amino acids, peptides, proteins, alditols, inositols, aldonic acids, uronic acids, aldaric acids, monosaccharides, disaccharides, cyclodextrins, chiral salts, chiral solvents, chiral acids, chiral bases and chiral esters 2) a water soluble polymer in amounts sufficient to form said two-phase system and 3) solvent consisting of water and at least one water-miscible organic solvent selected from the group consisting of dimethylsulfoxide, formamide and ethanolamine;
   b) mixing said two-phase system with a mixture to be separated;
   c) separating the two phases from each other.

34. The process of claim 33, wherein said mixture to be separated is a mixture of stereoisomers or optical isomers.

35. The process of claim 33, wherein said two-phase system further consists essentially of an affinity agent coupled to the water soluble polymer or phase forming compound or other carriers to be used in affinity partitioning.

36. The process of claim 33, wherein said mixing and separation steps accomplish a partition chromatography, wherein one of the phases of the two-phase system can be chemical bound or physically adsorbed to a solid support, and used as column material for chromatography separation.

37. The process of claim 33, wherein said mixing step b) is accomplished in a countercurrent distribution, cross-current extraction, counter-current extraction, liquid partition column chromatography or counter-current chromatography apparatus.

38. The process of claim 33, wherein the phase-forming compound is a chiral resolving agent selected from the group consisting of alditols, inositols, aldonic acids, uronic acids, aldaric acids, cyclodextrins and their derivatives.

* * * * *